United States Patent
Guadagno

(10) Patent No.: US 6,875,614 B2
(45) Date of Patent: Apr. 5, 2005

(54) OCCULT BLOOD TEST ENHANCER

(75) Inventor: Philip A. Guadagno, Vidor, TX (US)

(73) Assignee: Helena Laboratories, Corporation, Beaumont, TX (US)

( * ) Notice: Subject to any disclaimer, the term of this patent is extended or adjusted under 35 U.S.C. 154(b) by 0 days.

(21) Appl. No.: 10/466,174

(22) PCT Filed: Jan. 11, 2002

(86) PCT No.: PCT/US02/00622

§ 371 (c)(1),
(2), (4) Date: Jul. 14, 2003

(87) PCT Pub. No.: WO02/056029

PCT Pub. Date: Jul. 18, 2002

(65) Prior Publication Data

US 2004/0063211 A1 Apr. 1, 2004

Related U.S. Application Data

(60) Provisional application No. 60/260,920, filed on Jan. 12, 2001.

(51) Int. Cl.[7] .......................... G01N 33/72; G01N 21/77
(52) U.S. Cl. ........................... 436/66; 436/17; 436/164; 436/169; 422/61; 422/55; 422/56
(58) Field of Search ............................. 436/66, 63, 17, 436/164, 169, 131, 132; 422/61, 55, 56

(56) References Cited

U.S. PATENT DOCUMENTS

| | | |
|---|---|---|
| 3,996,006 A | 12/1976 | Pagano |
| 5,310,680 A | 5/1994 | Baker et al. |
| 5,391,498 A | 2/1995 | Baker et al. |
| 5,563,071 A | 10/1996 | Augurt |

OTHER PUBLICATIONS

Winawer, Sidney J., et al., "Colorectal Cancer Screening: Clinical Guidelines and Rationale", Gastroenterology, vol. 112, 612–15 (1997).

Hardcastle, Jack D., et al., "Randomised Controlled Trial of Faecal–Occult–Blood Screening for Colorectal Cancer", Lancet (North American Ed.), vol. 348, 1472–77 (1996).

Primary Examiner—Maureen M. Wallenhorst
(74) Attorney, Agent, or Firm—Jerold I. Schneider; DlA Piper Rudnick Gray Cary US LLP

(57) ABSTRACT

An improved fecal occult blood test having a matrix such as paper that is treated, imprinted or impregnated with a test reagent capable of undergoing a chromogen reaction is disclosed. The improvement relates to a novel developing solution in which the water to alcohol ratio is adjusted to enhance the sensitivity of the test.

17 Claims, No Drawings

OCCULT BLOOD TEST ENHANCER

This application claims priority from U.S. Provisional Application Ser. No. 60/260,920 filed Jan. 12, 2001. The entirety of that provisional application is incorporated herein by reference.

BACKGROUND OF THE INVENTION

1. Field of the Invention

The present invention relates to an improved fecal occult blood test having a matrix such as paper that is treated, imprinted or impregnated with a test reagent capable of undergoing a chromogen reaction. More particularly, the present invention relates to an improved developing solution for fecal occult blood tests.

2. Background of the Technology

Advances in medical science have led to the development of diagnostic tests for detecting various conditions. With many diseases, it is imperative that early diagnosis be made so that treatment may be administered when most effective.

The presence of occult (i.e., unseen) blood in fecal material has been found to be an early sign of gastrointestinal cancer. Frequently, when blood from internal bleeding becomes visible, the cancer has progressed to a late stage. Because early detection of gastrointestinal cancer is vital to successful treatment, it is important to detect the presence of blood before the blood from internal bleeding becomes visible in fecal material.

Specimen test slides and procedures for detecting fecal occult blood are well known. For example, U.S. Pat. No. 3,996,006 discloses slides having a specimen receiving sheet between a front panel and a rear panel, with openings in the panels and pivotal covers or flaps to cover these openings. The specimen receiving sheet is generally an absorbent paper printed or impregnated with a guaiac reagent.

In operation, a sample of fecal matter is smeared onto the guaiac paper through an opening on the front panel. The panel is then covered, and the flap of the rear panel is opened. A developing solution such as hydrogen peroxide is applied to the guaiac paper via the corresponding opening in the rear panel. Because guaiac is not soluble in water, traditional developing solutions for fecal occult blood tests include alcohol; therefore, the developing solutions have been referred to as "alcoholic peroxides." A typical formulation for such developing solutions is 5% hydrogen peroxide, 70% ethanol and 25% water. The water to alcohol (i.e., ethanol) ratio in such traditional developing solutions is, therefore, 25/70 or about 0.357.

If blood is present in the sample of fecal matter, the guaiac reaction will turn the paper blue. The guaiac, therefore, functions as a chromogen such that in the presence of hemoglobin (i.e., blood), which functions as a catalyst, oxygen is released from the developing solution, and the oxygen causes the guaiac to oxidize and change from essentially colorless to blue.

Tests for detecting blood in fecal samples before it is visible are extremely useful. Such tests, however, suffer from certain problems and deficiencies. One of the problems with the current fecal occult blood tests is the number of false negatives, i.e., negative test results in samples of bleeding patients. The test is not sensitive enough to pick up lower levels of blood in the feces.

Previous attempts have been made to increase the sensitivity of the test. For example, to detect smaller quantities of fecal occult blood, "enhancing" reagents have been included in the developer. These enhancers include parabens and tertiary amine compounds and their related analogues. For example, U.S. Pat. Nos. 5,310,680 and 5,391,498 disclose the use of phenolic-type compounds such as esters of hydroxybenzoic acid, as well as phenol, guaiacol, 3,5-dimethylphenol, methyl salicylate, 3,5-dichlorophenol, paranitrophenol and parabromophenol. It is arguable whether these enhancers actually change the sensitivity or merely make the chromogenic reaction, i.e., the color change of the guaiac, more readily visible.

Hydration of the smear prior to development has also been employed in an attempt to increase the sensitivity. While it has been suggested that hydration provides greater sensitivity, no meaningful data is available as to the amount of hydration. Furthermore, according to U.S. Pat. Nos. 5,310,680 and 5,391,498, hydration adversely affects the specificity of the test, particularly by producing unacceptable false positive rates, i.e., positive reactions without fecal occult blood present, by reacting with other interfering substances such as vegetable peroxidases.

A need still exists, however, for fecal occult blood tests with greater sensitivity.

SUMMARY OF THE INVENTION

It has now been found that increased sensitivity of fecal occult blood tests can be achieved by a totally different approach, thereby eliminating the need for parabens, tertiary amine compounds or other enhancers. More specifically, it has now been found that the desired sensitivity can be achieved by adjusting the water to alcohol ratio of the developing solution. It has also been discovered that by varying the concentration of the alcohol in the developing solution, hemoglobin detection limits are affected.

It is, therefore, an object of the present invention to increase the sensitivity of the test for fecal occult blood. Increasing the sensitivity includes both detecting lower levels of blood in the feces and obtaining greater readability, i.e., obtaining a clearer and deeper blue color with the same concentration of test reagent or chromogen.

It is also an object of the present invention to provide a fecal occult blood test developing solution having variable hemoglobin detection limits.

In accordance with the present invention, there is provided a method of enhancing the sensitivity of a fecal occult blood test having a matrix containing a test reagent that is capable of undergoing a chromogen reaction. The method generally comprises adjusting the water to alcohol ratio of the developing solution.

In accordance with the present invention, there is also provided an improved developing solution for determining fecal occult blood in a sample using a test matrix containing a test reagent capable of undergoing a chromogen reaction. The solution comprises hydrogen peroxide, an alcohol and water. The water to alcohol ratio depends upon the alcohol used in the developing solution.

The objects, advantages and features of the present invention will become more apparent from the following detailed description of the presently preferred embodiments, including the appended claims.

DETAILED DESCRIPTION OF THE INVENTION

The present invention includes a method of enhancing the sensitivity of a fecal occult blood test having a matrix containing a test reagent that is capable of undergoing a chromogen reaction. The matrix is preferably an absorbent paper and is treated, imprinted or impregnated with a test reagent capable of undergoing a chromogen reaction. Preferably, the test reagent is guaiac. The method generally comprises adjusting the water to alcohol ratio of the developing solution used in executing the fecal occult blood test.

The present invention, therefore, also includes an improved developing solution for determining fecal occult blood in a sample using a test matrix containing a test reagent capable of undergoing a chromogen reaction. Again, the matrix is preferably an absorbent paper and is treated, imprinted or impregnated with a test reagent capable of undergoing a chromogen reaction. Preferably, the test reagent is guaiac.

While not wishing to be bound to any one theory, it appears that the present invention increases the visibility of the chromogen reaction. The invention appears to cause the part of the reaction, which has turned blue, to migrate (generally radially) away from the stool. In other words, the blue chromogen capillates or migrates outwardly. This makes it more visible because it is not obscured by the dark colored stool samples.

The improved developing solution generally comprises hydrogen peroxide, water and alcohol. The alcohol may be any of the lower aliphatic alcohols such as methanol, ethanol, propanol and isopropanol. The preferred alcohol is propanol. If a higher order alcohol such as, for example, butanol, are used, the alcohol appears to denature the blood (which is water soluble), and the proper reaction is not obtained, even if blood is present in the sample. The more polar the alcohol, the more it is like water. The less polar the alcohol, the less it is like water.

The improvement to the developing solution results from adjusting the water to alcohol ratio of the developing solution such that the desired sensitivity can be achieved. By adjusting the water to alcohol ratio in accordance with the present invention, no enhancing agents are necessary in the developing solution.

The water to alcohol ratio depends on the specific alcohol present in the developing solution. Table 1 presents the general ranges of the water to alcohol ratio for methanol, ethanol, propanol and isopropanol. Upon progressing from methanol to ethanol to propanol to isopropanol, one might expect there would be some linearity of response. Surprisingly, as seen in Table I, this is not the case. Instead, the ratios are non-linear when progressing among the lower aliphatic, water-soluble alcohols from methanol to ethanol to propanol to isopropanol.

TABLE 1

| Alcohol | Lower Water to Alcohol Ratio | Upper Water to Alcohol Ratio |
| --- | --- | --- |
| Methanol | 0.13 | 0.75 |
| Ethanol | 1.14 | 1.75 |
| Propanol | 0.93 | 1.42 |
| Isopropanol | 1.14 | 1.42 |

Generally, the optimum, or most preferred, water to alcohol ratios are approximately mid-range of the data shown in Table 1. In that case, the optimum water to alcohol ratio for ethanol (i.e., about 1.445) is more than four times the traditional water to alcohol ratio (i.e., 0.357). If propanol is used, then the most preferred ratio of water to propanol is about 1.15, which is over three times the traditional (ethanol) ratio. If methanol is used, the most preferred water to alcohol ratio is about 0.34.

The paper matrix may include built-in positive and negative controls. Varnish may or may not be used in connections with the controls. If the matrix includes such controls, and the controls include varnish, then guanidine hydrochloride (approximately 1% or less) may be included in the developing solution to effectively dissolve the varnish. If controls not containing varnish are present, then no guanidine hydrochloride is required.

In a preferred embodiment, the fecal occult blood test developing solution comprises about 44.6 g/g n-propanol, about 51.4 g/g water, about 3.9 g/g hydrogen peroxide (30%) and up to 0.5 g/g guanidine hydrochloride.

While the invention has been described in conjunction with specific embodiments, there are many alternatives, modifications and variations that will be apparent to those skilled in the art in light of the foregoing description. The invention is intended to embrace all such alternatives, modifications and variations that fall within the scope of the appended claims.

What is claimed is:

1. In a method for detection of occult blood in sample by a chromogenic reaction including the steps of depositing a sample on a chromogen matrix and applying a developing solution which includes water and alcohol in a water to alcohol ratio, the improvement comprising adjusting the water to alcohol ratio of the developing solution to a level that enhances the visibility of the chromogenic reaction.

2. A method according to claim 1, wherein the alcohol is selected from the group consisting of methanol, ethanol, propanol and isopropanol.

3. A method according to claim 2, wherein the alcohol is methanol and the water to alcohol ratio is adjusted to be within the range from about 0.13 to about 0.75.

4. A method according to claim 2, wherein the alcohol is ethanol and the water to alcohol ratio is adjusted to be within the range from about 1.14 to about 1.75.

5. A method according to claim 2, wherein the alcohol is propanol and the water to alcohol ratio is adjusted to be within the range from about 0.93 to about 1.42.

6. A method according to claim 5, wherein the alcohol is n-propanol and the water to alcohol ratio is about 1.15.

7. A method according to claim 2, wherein the alcohol is isopropanol and the water to alcohol ratio is adjusted to be within the range from about 1.14 to about 1.42.

8. In a method for detection of occult blood in a sample, including the steps of depositing a sample on a chromogen matrix and applying a developing solution which includes water and alcohol in a water to alcohol ratio, the improvement comprising enhancing the sensitivity of detection by adjusting the water to alcohol ratio of the developing solution, and wherein the water to alcohol ratio is adjusted to be within the following ranges:

a) when the alcohol is methanol, the water to alcohol ratio is adjusted to be within the range from about 0.13 to about 0.75;

b) when the alcohol is ethanol, the water to alcohol ratio is adjusted to be within the range from about 1.14 to about 1.75;

c) when the alcohol is propanol, the water to alcohol ratio is adjusted to be within the range from about 0.93 to about 1.42;

d) when the alcohol is isopropanol, the water to alcohol ratio is adjusted to be within the range from about 1.14 to about 1.42.

9. A method according to any of the preceding claims, wherein the chromogen is guaiac.

10. A method according to claim 9, wherein the developing solution is flee of parabens, tertiary amine compounds and their related analogues.

11. A method according to any one of claim 1, 2, 3, 4, 5, 7, 6, or 8, wherein the developing solution is free of parabens, tertiary amine compounds and their related analogues.

12. A test kit for determining the presence of occult blood in a sample comprising the chromogen and the developing solution according to any one of claim 1, 2, 3, 4, 5, 7, 6 or 8.

13. A test kit according to claim 12, wherein the chromogen is guaiac.

14. A test kit according to claim 13, wherein the developing solution is free of parabens, tertiary amine compounds and their related analogues.

15. A test kit according to claim 12, wherein the developing solution is free of parabens, tertiary amine compounds and their related analogues.

16. A developing solution for developing a sample that has been deposited on a chromogen matrix to detect occult blood, the developing solution including alcohol and water according to any one of claim 2, 3, 4, 5, 7, 6 or 8.

17. A developing solution according to claim 16, wherein the developing solution is free of parabens, tertiary amine compounds and their related analogues.

* * * * *